(12) United States Patent
Nelson et al.

(10) Patent No.: US 8,672,996 B2
(45) Date of Patent: Mar. 18, 2014

(54) SELF-EXPANDING MEDICAL DEVICE

(75) Inventors: Kevin D. Nelson, Richardson, TX (US);
Paula J. Taylor, Cedar Hill, TX (US);
Brent B. Crow, Grand Prairie, TX (US)

(73) Assignee: TissueGen, Inc., Dallas, TX (US)

( * ) Notice: Subject to any disclaimer, the term of this patent is extended or adjusted under 35 U.S.C. 154(b) by 0 days.

(21) Appl. No.: 13/059,968

(22) PCT Filed: Aug. 19, 2009

(86) PCT No.: PCT/US2009/054345
§ 371 (c)(1),
(2), (4) Date: Mar. 29, 2011

(87) PCT Pub. No.: WO2010/022173
PCT Pub. Date: Feb. 25, 2010

(65) Prior Publication Data
US 2011/0172755 A1    Jul. 14, 2011

Related U.S. Application Data

(60) Provisional application No. 61/090,162, filed on Aug. 19, 2008.

(51) Int. Cl.
*A61F 2/88* (2006.01)
(52) U.S. Cl.
USPC ........................................... 623/1.22

(58) Field of Classification Search
None
See application file for complete search history.

(56) References Cited

U.S. PATENT DOCUMENTS

| | | | |
|---|---|---|---|
| 6,514,285 B1 * | 2/2003 | Pinchasik | 623/1.22 |
| 2001/0004683 A1 | 6/2001 | Gambale et al. | |
| 2002/0062147 A1 | 5/2002 | Yang | |
| 2004/0133266 A1 * | 7/2004 | Clerc et al. | 623/1.22 |
| 2004/0186556 A1 | 9/2004 | Hogendijk et al. | |
| 2007/0208416 A1 * | 9/2007 | Burpee et al. | 623/1.22 |
| 2007/0282425 A1 * | 12/2007 | Kleine et al. | 623/1.15 |

OTHER PUBLICATIONS

International Search Report; mailed Oct. 6, 2009; Authorized Officer: Blaine Copenheaver.

* cited by examiner

*Primary Examiner* — Thomas J Sweet
*Assistant Examiner* — Rebecca Preston
(74) *Attorney, Agent, or Firm* — Winstead PC

(57) ABSTRACT

The invention relates to a helical coil comprising multiple reversing sense helical coil units that are capable of drug elution, come in lengths appropriate for long, diffuse lesions, have the ability to have a step-wise tapering diameter, and provide all the benefits of a small closed cell stent design while maintaining high flexibility, high radial force and crush resistance due to an underlying helical coil.

16 Claims, 5 Drawing Sheets

SELF-EXPANDING MEDICAL DEVICE

CROSS-REFERENCES TO RELATED APPLICATIONS

This Application is a U.S. National Stage Application of International Application No. PCT/US09/54345, filed Aug. 19, 2009, and claims priority from U.S. Provisional Patent Application No. 61/090,162, filed Aug. 19, 2008 which is hereby incorporated by reference as if fully set forth herein.

TECHNICAL FIELD OF THE INVENTION

The invention relates to a helical coil-containing device comprising multiple reversing sense helical coil units that are capable of drug elution, which come in lengths appropriate for long, diffuse lesions, have the ability to have a step-wise tapering diameter, and provide all of the benefits of a small closed cell stent design while maintaining high flexibility, high radial force and crush resistance due to an underlying helical coil.

BACKGROUND OF THE INVENTION

There is a need for medical devices that can be placed in tubular organs of the human or mammalian body that are self expanding and can stay in place. These medical devices can serve a number of purposes. For example, they can act as a stent to maintain the body lumen, or they can act to hold or anchor other devices such as filters or indwelling catheters. The use of stents to maintain the patency of bodily lumens is well known. Stents are typically delivered in an unexpanded configuration via a catheter to a desired bodily location. Once at the desired bodily location, the stent is expanded and implanted in the bodily lumen. The stent may self-expand or may be mechanically expanded.

Self-expanding stents or medical devices are fabricated larger than the size of the lumen by some amount so that, once implanted into the lumen, the stent exerts some amount of radially outward force on the lumen as it seeks to return to its as-fabricated configuration. Self-expanding devices are subject to high stresses when the diameter is reduced down onto the catheter for insertion into the body; these stresses are largely relieved when the stent is released inside the body lumen. The delivery means such as a delivery catheter for a self-expanding device must be capable of holding the stent in this high stress configuration until it releases the device inside the body lumen. This is usually accomplished by retention devices on the delivery means such as a retractable sheath, retention wires, clips, or other mechanical means capable of resisting the forces due to the internal stress in the device. The delivery means must be capable of releasing the device in a controlled way such that the desired final position of the stent within the body lumen is accurately maintained.

Devices that are mechanically expanded are fabricated to be just slightly larger than the delivery means, and after insertion into the body cavity are subject to large forces that plastically deform the device to a new size inside the body lumen. The force may be applied via an expandable member such as a balloon or via any other mechanical device.

Devices are used in an array of hollow body cavities including arteries and veins, such as the coronary arteries, the peripheral arteries, arteries of the neck, and cerebral arteries. They may also be used in non-blood contacting spaces such as, biliary ducts, urethras, ureters, fallopian tubes, bronchial tubes, the trachea, the esophagus, and within the digestive tract and the prostate.

For devices used in the peripheral vascular system, the physiological deformations exerted by the body on the device are substantially different from those experienced by a stent in the coronary arterial system. For example, in the arteries of the leg, specifically the superficial femoral artery, there are substantial axial, torsional, and flexing deformations that have no counterpart in the coronary arterial system. This means that the same device designs that work in the coronary arteries are not necessarily going to work optimally in the arteries of the leg.

Previous groups have used coil-based stents or devices with limited clinical success. The purpose of the claimed invention is to address and correct the problems with previous generations of coil-based devices. Prior generations of coil stents fall into three groups. The first group consists of stents that are composed of a single fiber wound in an unbroken helical coil of uniform diameter and even spacing (that is, the number of turns of the coil/cm is a constant value). The second group is a rather unique design, again consisting of a single fiber wound into a coil-based design, but where the winding sense of the coil changes direction (right hand thread to left hand thread) at regular intervals. Finally, the third group (and clinically the most successful to date) is composed of multiple fibers, each of which is individually a helical coil, yet they are woven or braided together in such a way as to make a highly flexible, closed cell design.

The following discussion is directed to the first two groups mentioned above. The specific clinical problems encountered to date by various devices within these two groups of coil-based devices are listed below:
 a. Tissue prolapse between the coils, i.e. insufficient coverage of the vessel wall
 b. High rates of restenosis
 c. Difficult to deliver, i.e. long delivery times and typically awkward delivery catheters
 d. Inaccurate placement due to dramatic jumping of the stent upon delivery, and/or different lengths of the stent on and off the catheter.
 e. Stent migration post deployment
 f. Limited to short stent lengths
 g. Collapse of the stent under shear load
 h. Limited to constant diameter stents All coil-based devices should be designed to reduce restenosis, have high biocompatibility, and a low profile. Further, all such devices must be accurately placed and easy to deliver. In addition to these general requirements, devices used in the arteries of the leg also require mechanical compliance in axial extension and compression, flexion and torsion while maintaining radial stiffness.

The design criteria for a device appropriate for peripheral vascular circulation, and the solution arrived at, forms the basis for the claimed invention. The invention is a helical coil design consisting of multiple reversing sense helical coil units, that are capable of drug elution, come in lengths appropriate for long, diffuse lesions, have the ability to have a step-wise tapering diameter, and provide all the benefits of a small closed cell design while maintaining high flexibility, high radial force and crush resistance due to the underlying helical coil.

Although the claimed invention is appropriate for the peripheral vascular system, the invention itself is much broader in scope and can be applied to a large number of medical devices. Any medical device that is required to maintain position within any tubular anatomical structure can benefit from this invention.

SUMMARY OF THE INVENTION

An embodiment of the invention is directed to a device for placement in a lumen, where the device comprises one or more segments, wherein each segment comprises two coils of opposing winding sense and each segment is connected to another segment by a first structure, wherein the first structure changes the winding sense of the coils, such that a coil of one winding sense is connected to the first structure and a coil of an opposite winding sense is connected to the first structure, and wherein the first structure extends into or partially fills the gap created by the divergence of the coils connected to the first structure.

A further embodiment of the invention is directed to a system comprising a delivery means, wherein the delivery means is removably connected to one or more devices according to the claimed invention.

BRIEF DESCRIPTION OF THE DRAWINGS

FIG. 7 shows a 45 degree rotation of the device of the invention from FIG. 6. It is shown to illustrate how in this embodiment, the link structure is formed from, and is continuous with the fibers used to form the helical coils of the device. This is appreciated as the joining part of the two helical coils is welded together as a crossing point, but the fibers continue on with similar pitch as they begin to fill the space created as left and right hand coils diverge.

FIG. 8 shows a 90° rotation of the same device shown in FIG. 7. This is a view of the link structure in the center containing two dark rectangles. These rectangles are used as an aid to radiopacity and are not a part of this invention. All of the structure seen in the middle is the rotating link of the device.

FIG. 9 shows an approximate 90° rotation of FIG. 8 and shows the continuation of the link around the back side of the device, filling in the widening gap between the left hand and right hand fibers.

FIG. 10 shows the terminal end of the link structure in this embodiment. One can appreciate that the weld part of where the left hand and right hand fibers were welded together to initiate the link structure is about 180° from the terminal end of the link structure shown here. This terminal part of the link structure shows a "dove tail" shape. The dove tail shape in this embodiment is used to attach the device to the delivery catheter, although many other means of attachment are possible and should all be considered within the scope of this invention.

Figure 1:
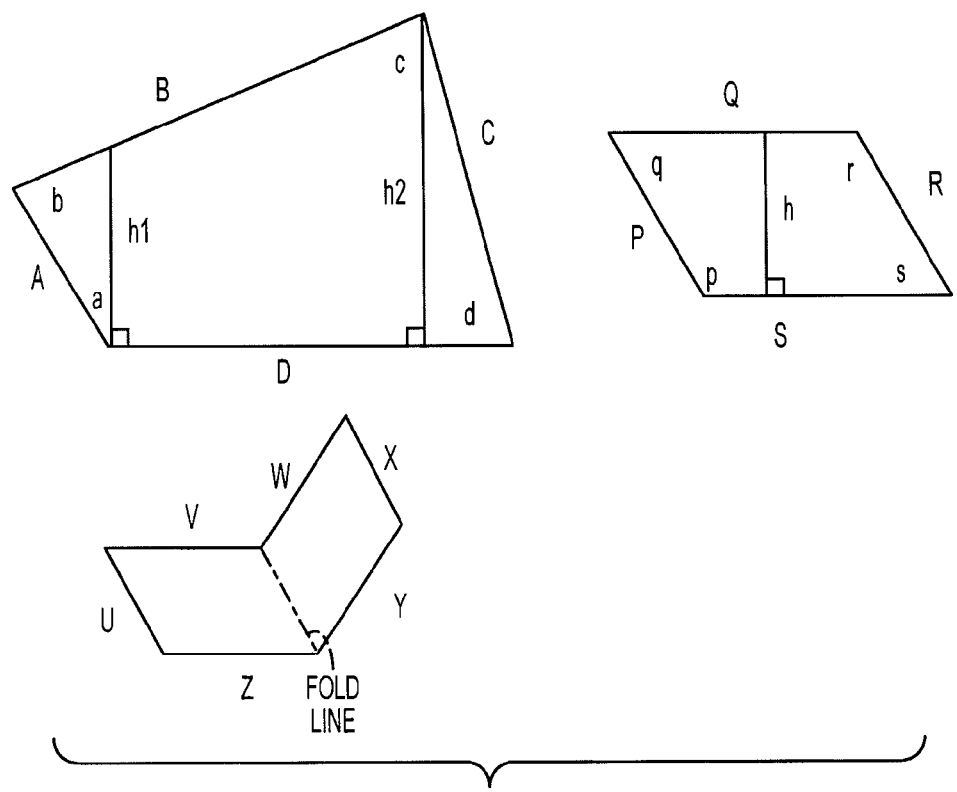
FIG. 1 represents a mesh having a quadrilateral shape; general quadrilateral ABCD with interior angles abcd, and parallelogram PQRS with corresponding interior angles pqrs and chevron UVWXYZ. In the case of tapered device, the height of the quadrilateral at end A is h1, and corresponds to the circumference of the lumen at end A, and height h2 at end C corresponds to the circumference of the lumen at end C. The interior angle "a" is supplementary to the pitch angle of the helical coil or link structure at end A, which may or may not be the same as the pitch angle "d" at end C. In the special case of constant diameter device, the general quadrilateral reduces to a parallelogram wherein the angle "s", which is supplementary to angle "p", is the pitch angle of the helical coil and height h is the same as the circumference of the lumen. The length of the quadrilateral mesh section is taken as the length of the line connecting the midpoint of A to the midpoint of C, on the parallelogram it is simply the length of S or Q. If chevron UVWXYZ is folded along the fold line, it becomes a parallelogram wherein sides U and X become coincident as well as V and W and Y and Z.
Figure 2:
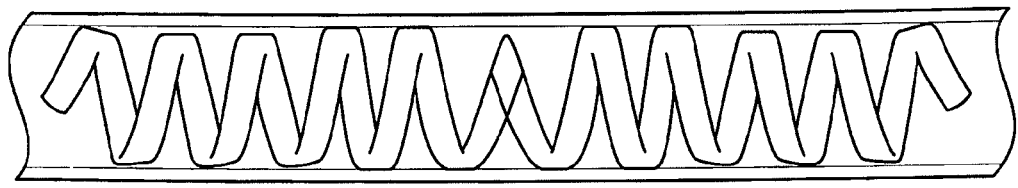
FIG. 2 shows a single segment of a medical device of the invention with the link structure removed for visualization of the joining together of right hand and left hand helical coils.
Figure 3:
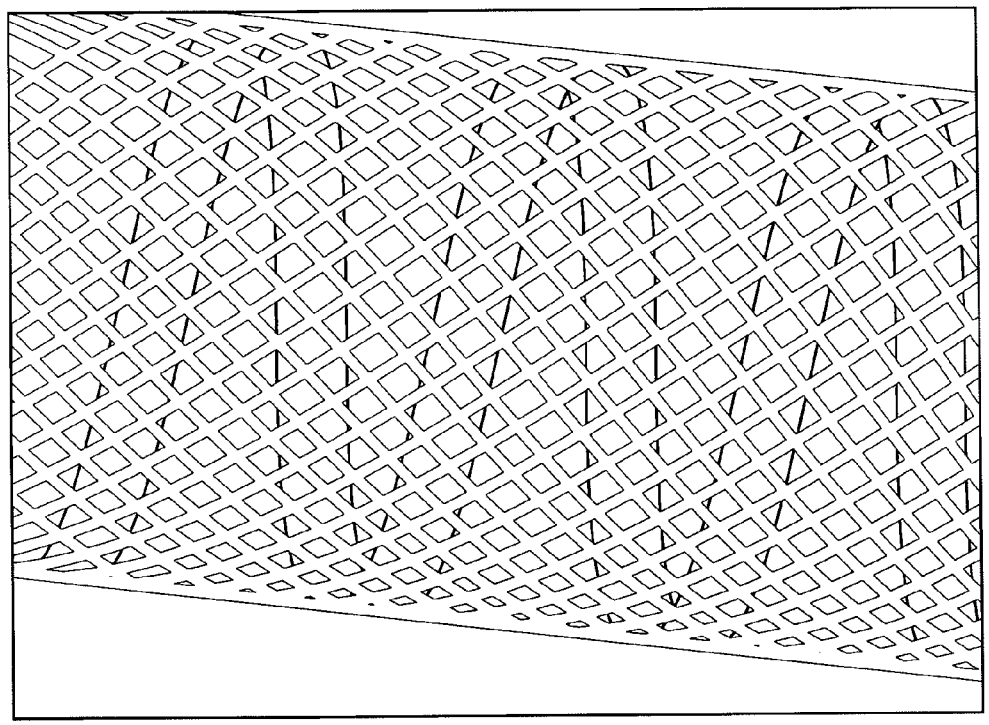
FIG. 3 shows a mesh covering part of a device of the invention.
Figure 4:
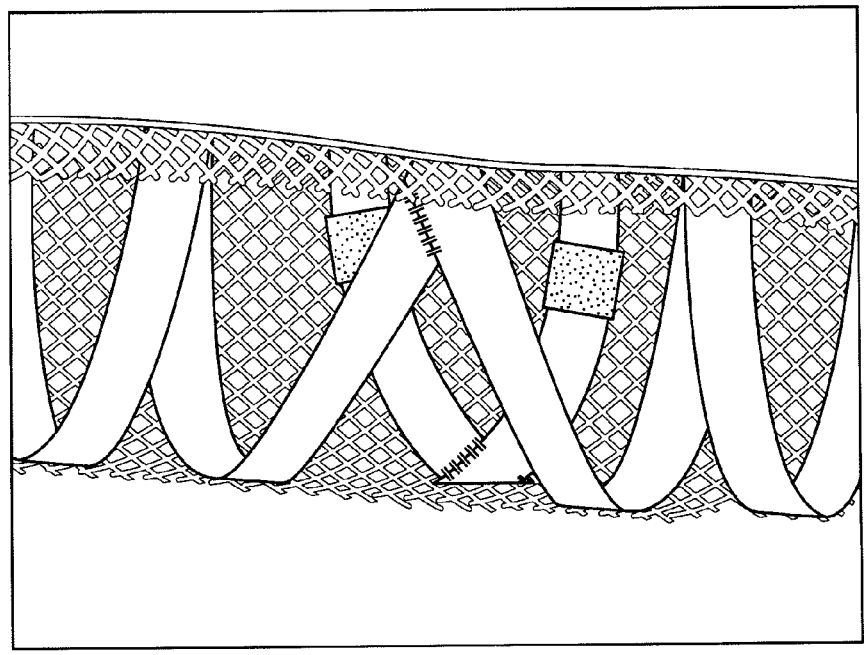
FIG. 4 shows the open side of the device of the invention where the non-encompassing mesh is not covering the device in its fully expanded configuration.
Figure 5:
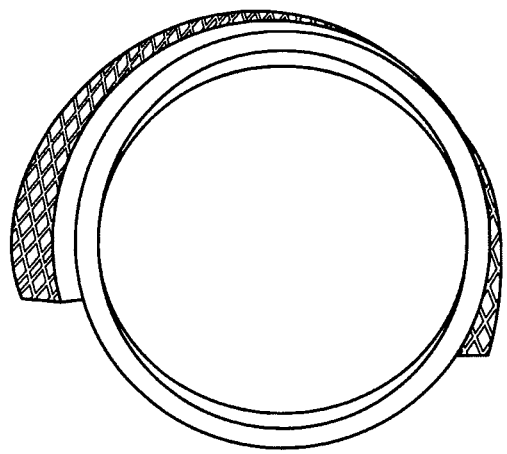
FIG. 5 shows the device looking down the axis of the device. The mesh is seen covering slightly more than half the device in its fully expanded form. This is a 90° rotation from FIG. 4.
Figure 6:
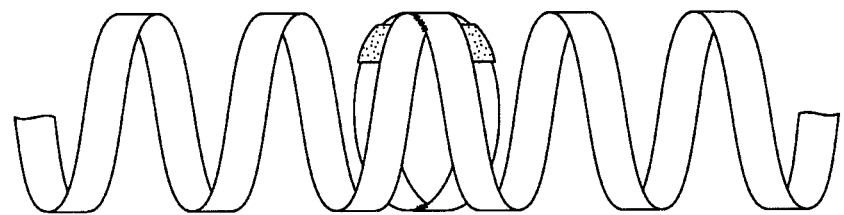
FIGS. 6-10 show rotations of a single device of the invention made according to an embodiment of the invention. Prominent in the view of FIG. 6 (center of figure) is a cross over point where the two left hand and right hand helical coils of this segment join together. In this embodiment they are welded together and the link structure extends above this welded point. The device is shown to rotate about its longitudinal axis in FIGS. 7-10 to illustrate the link structure of this embodiment.
Figure 7:
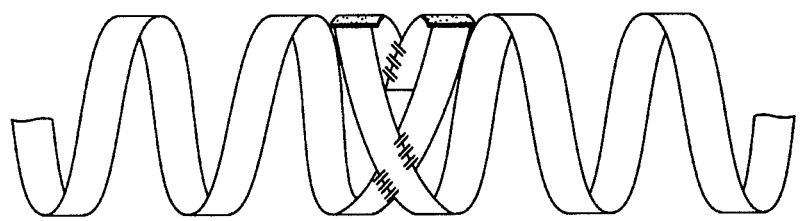
Figure 8:
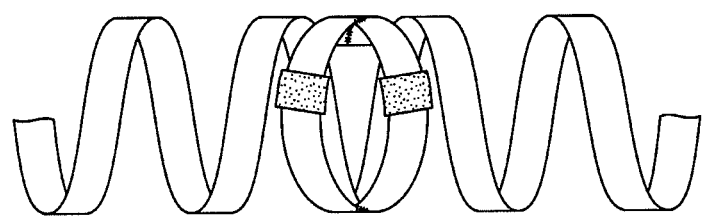
Figure 9:
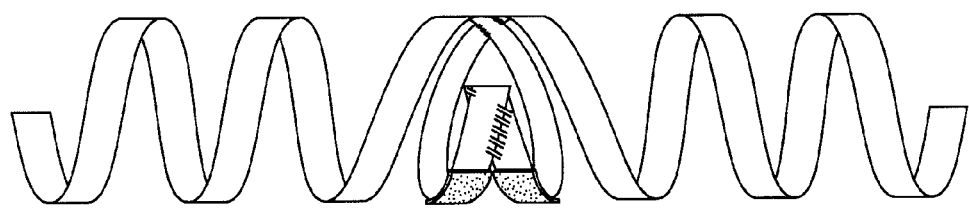
Figure 10:
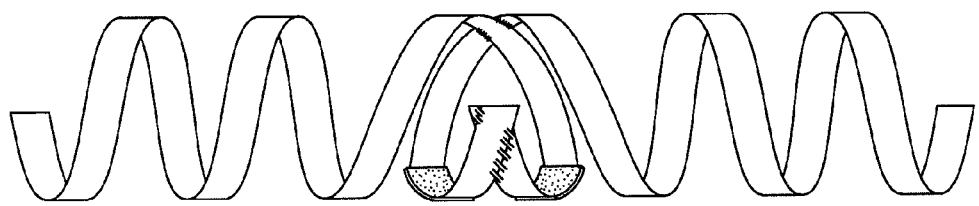

It is noted that FIGS. 6-10 show small metallic sleeves over the center point of the rotating link that are dominantly displayed in these figures. In the embodiment shown, the sleeves are made from platinum iridium, and are placed on the stent for radiopacity. There are other means of creating radiopacity, that are well known to those skilled in the art, such as other types of markers, also including adding radiopaque agents in the polymer.

DETAILED DESCRIPTION OF EXEMPLARY EMBODIMENTS

As used herein the term "device" or "medical device" or "stent" refers to a coiled structure that may be placed within a lumen or organ of a human or animal. The devices of the invention can serve any number of functions including, but not limited to, structural support, drug delivery, and maintenance of the patency of a cavity or lumen. The coiled structures within a lumen can also serve to anchor other medical appliances such as filters, and in-dwelling catheters, etc. within the lumen.

As used herein, the term "coil" refers to a spiraling loop containing a real number multiple of complete revolutions.

Medical devices of the invention are composed of two general types of structures: one or more fibers wound in helical coils, and link structures that connect two helical coils of opposite winding sense. As used herein, the term "fiber" is used throughout to identify an elongated member used to create the helical coils, whose length (if unwound from the coil shape) is typically greater than any other physical dimension. By use of the term "fiber" we make no assumptions about the type of material that can be used. For example, any type of metal, any metal alloy, or any shape memory alloys; any polymers, blends or copolymers; or any ceramics may be used to form a fiber of the invention. Additionally, the fibers of the invention can be round, oval, rectangular or of any other cross-sectional shape. In fact, a preferred embodiment does not use a circular cross section. Fibers of the invention include extruded members, but certainly one could envision a hollow tube with parts cut out leaving a residual form of a helical coil, for example, which would also be included in the concept of the term "fiber" as used herein.

The link structures are defined below, but can be comprised of fibers as previously defined, or can be of any other material or design. A purpose of link structures is to connect helical coils of opposing winding senses (left hand and right hand). Therefore, the link structures may either be composed of or be continuous with the fiber(s) of the helical coils, or may bond with the fibers of the helical coils. All of the link structures of the devices of the invention need not have the same design as will be explained below.

A fiber of the invention, whose cross section is preferably non-circular, is shaped in a helical coil (either left or right hand oriented) for some number of turns, thus creating an open lumen. There is no restriction to the number of turns that comprise a helical coil. Mathematically, a helical coil is defined as any structural member whose x, y and z coordinates can be parametrically described by a radius r and an angle θ using the following parametric equations: x=r cos(θ); y=r sin(θ); and z=cθ, where c=L/(2πn), where L is the length of the helical coil, and where n is the number of turns in the coil. The invention does not limit use of the term "coil" to instances where θ>2π. Thus, partial loops are permitted, i.e., n is allowed to be both greater than or less than 1. Coils of this invention include those that strictly follow the above mathematically defined criteria; however, it should be understood that variations of such coil, for example, but not limited to allowing "c" to be expressed as a function rather than a constant are within the scope of this invention. Other variations including, but not limited to, the fiber in its unwound condition having a specific curvilinear shape are also within the scope of this invention. One such possibility is to create a fiber whose shape before creating the coil is periodic in some way, such as sinusoidal, sawtooth, square wave or any other such curve. The periodicity may be constant or variable, meaning that the amplitude, period, or phase may change over the length of the fiber. When such a fiber with either constant or variable periodicity is then wound around a mandrel to create the helical coil of this invention, the material location of the fiber at any given point will not be found by the above parametric definition of a helical coil. However all such specific cases are considered to fall within the scope and intent of this invention.

In order to reverse the winding sense of the device, the fiber of a first helical coil either forms, or is attached to, a link structure. A second helical coil of opposite winding sense with respect to the first helical coil either attaches to, or emanates from, the link structure and continues to lengthen the open lumen for the same or different number of turns as the first helical coil. This fundamental unit of two helical coils of opposite winding sense joined by a link structure is the basic element of the devices of the invention, and is called a segment. The segment is composed of two helical coils that are co-axial (in line) and have opposite winding directions (one is a left hand coil and the other is a right hand coil). The coils are joined end to end, by a linking structure, herein called a rotating link. The two joined coils represent one segment of the device. Multiple segments can be placed end to end to form one complete device. There is no theoretical limit to the sizes of the individual segments, nor to the number of segments that can be joined. Segments are always linked together by a link structure herein referred to as a stationary link.

The segments must be joined in such a way as to preserve the alternating order of the winding directions. For example if the first segment of the device is ordered left hand coil (L) then right hand coil (R) as one looks at the device starting from the end closest to the user after attaching it to the delivery catheter and moving further away, then the order LR must be preserved in all subsequent segments, such that the final arrangement of the device is LRLRLR . . . etc, and no two segments can put two left hand coils nor two right hand coils next to each other.

Multiple segments may be joined together using link structures. The link structure (or first structure) that joins segments together are referred to as "stationary links". The two helical coils comprised within a segment are generally co-axial, but are not required to be. The link structure (or second structure) that joins two opposite-sensed helical coils within a segment is referred to as a "rotating link". Rotating and stationary links may be of the same or different designs, but in both cases always connect helical coils of opposite winding sense. As one starts at the end of the medical device, which when mounted on the delivery means is then closest to the person implanting the device, the first link is numbered 1, and is always a rotating link. If the medical device is composed of multiple segments, then odd numbered links 1, 3, 5 etc are rotating links, while even numbered links are stationary links. Note that there will always be an odd number of total links.

All stationary links have at least the following requirements—(1) the link structure must reverse the sense of the coil (changing from a right hand coil to a left hand coil or visa versa); (2) the link structure must largely fill in the gap created as left hand and right hand fibers diverge further apart. This is because the two coils will be seen to be diverging if one rotated the device about its longitudinal axis. This widening gap between diverging coils, if left unfilled by the link structure, could lead to unacceptable clinical outcomes; (3) the link structure must exert force on the body lumen pushing the coil ends joined by that link against the luminal wall; and, (4) the link structure must provide a means of attachment to the delivery catheter. The rotating links are required to reverse the direction of the joined helical coils and must also provide a means of attaching the medical device to a delivery mechanism. They may, but are not required to, fulfill the other requirements of stationary links.

In any given device of the invention, rotating and stationary links are capable of having the same design, but do not necessarily have to. The terms rotating and stationary as applied to the links originate from their attachment to the delivery catheter. Rotating links and stationary links need not have the same geometry or design. Adjacent segments do not need to be of the same size, in either diameter or length. Within one segment, the two coils can also be of different size in terms of both diameter and length. There are no restrictions on the number of turns the coil can or should have in each coil of any segment. Indeed, for tapered devices, the number of turns and diameter will potentially differ both within a single segment and across segments.

It is also within the scope of the invention for each of the helical coils and the links to be made of different materials. They may optionally be made of a shape memory material, for example nitinol. Other types of metals such as cobalt chromium alloys, stainless steel, other metals and alloys, polymers, ceramics and the like may also be used in the construction of the helical coils and the links.

The terminal ends of the invention may be continuous with the coil, or may be constructed with a distinct change in direction with reference to the direction of the helical coil. This change in direction may be necessary for the delivery catheter system to grip the medical device to allow proper loading and release. The distinct angle change may consist of straight segments or in certain embodiments contain terminating curves, loops or hairpin turns. In one preferred embodiment, these end segments, of any geometry, are for the purpose of attaching the medical device to the delivery means.

The cross sectional shape of the fiber used to construct the helical coil may be round, oval, or of any other shape. The fiber itself may contain therapeutic agents, have a coating that contains drugs, or have no drugs at all. As used herein, the term drugs is used to refer by reference and example to the entire American Pharmacopia as valid but non-limiting examples of drugs that may be loaded therein. The fiber may also contain biologically active species such as proteins, growth factors, cytokines, enzymes, chemokines, anti-bodies, nuclear proteins such as transcription factors, or any other molecules consisting of peptides, oligopeptides, or sections containing nucleic acids such as double or single stranded RNA or DNA. The fibers could also include polysaccharides with or without attached proteins or other amino acid or nucleic acid groups. Also within this group are molecules or assemblies of molecules that are designed to mimic the function of such above named molecules, such as biosimilars, bioMems and the like In a preferred embodiment of the invention, one or more non-expanding, non-circumferential meshes are attached to the coil or link structure of the device. The shape of each mesh is a quadrilateral in that in the most general case, no two legs are required to be the same length, nor are any two sides required to be parallel. However, in the case of a constant diameter device, the quadrilateral will reduce to a parallelogram as shown in FIG. 1.

In the case of a constant diameter device, the height of the parallelogram has the same measurement as the circumference of the target bodily lumen. The length of the mesh is such that the sum of all lengths of all attached meshes is greater than or equal to the overall end to end length of the device. For example in a preferred embodiment, there may be four meshes attached to a constant diameter device. The height of all four mesh parallelograms is the same, and is equal to the target lumen circumference, and the lengths of the mesh parallelograms are all approximately ¼ the overall (end to end) length of the device. There may be some amount of axial overlap of the mesh components, and hence, the sum of the lengths of the mesh pieces may, in most embodiments, exceed the overall designed length of the device. The mesh sections are attached in such a way that when the device is within the body lumen the mesh segments cover the lumen with some amount of axial and radial overlap allowed. The medical device is free to rotate or move relative to the mesh sections except at these attachment points.

Another aspect of this invention is the potential use of the mesh as a drug delivery reservoir. This can be accomplished in two ways. First, a therapeutic agent (as used for fibers of the helical coils) can be within the strands of the mesh, or as a coating on the outside of the strands, or in a preferred embodiment, loaded into a hydrogel or other material that is held in place between the strands of the mesh, or any combinations of these methods of loading drug into the mesh. Each of these methods of loading the mesh with drug provides varying release kinetics of the contained drug.

The method of manufacturing the device of the invention will depend in large measure on the type of material from which it is comprised. In an embodiment, the fiber comprising the medical device is made from a polymer that has shape memory capabilities. In this case, the polymer may be wound around a mandrel, the mandrel having features that allow the polymer fiber to reverse direction and form appropriate link structures. Typically, the mesh is attached to the device while still upon the mandrel for ease of fabrication. The mandrel with the polymer fiber and mesh is then treated in such a way as required for the polymer to permanently take the shape of the mandrel. Frequently, this will be accomplished through heating and cooling the mandrel and polymer fiber. After the shape memory process, the medical device is cut to appropriate lengths and removed from the mandrel. The device is now ready to be loaded onto a delivery catheter for the next phase of processing, which may typically be packaging, sterilization, and shipping.

Although heat treatment is included in the above embodiment as a means of setting the shape of the polymer fiber, this example is not intended to be limiting and other methods of setting a shape in the polymer fiber may apply. For example chemical, electrical, irradiation or mechanical means are possible depending on the material used in creating the fiber. Clearly, metals and ceramics will require different shape-setting processes than a polymer.

In another preferred embodiment, the raw material can start as a solid hollow tube, and the coil and connecting links are cut by laser or other means from the solid tube. For certain materials, such as, for example, nitinol, this method of production may be preferred.

The invention is also directed to methods of deploying any of the inventive medical devices disclosed herein at a desired bodily location. In accordance with an embodiment of the invention, a medical device delivery catheter comprising any of the inventive medical devices disclosed herein is provided. In an embodiment, the medical device is attached to the delivery catheter at the distal and proximal ends, and at all link structures, both rotating and stationary. The delivery catheter provides relative rotation between each adjacent attachment point. This winding motion across the helical coils of the medical device causes the coils to reduce in diameter, thus winding the medical device down to a smaller diameter in preparation for insertion into the body through an introducer, as would be familiar to those skilled in the art. The terminal ends of the medical device and each of the link structures are designed such that the delivery catheter can maintain its grip on the medical device under these high torsion loads, yet with the requirement that, as the device unwinds and the torsional stress is reduced, the catheter is able to maintain its hold on the device until such time as release is desired, and must be capable of completely releasing the medical device. The design of the terminal end pieces and links is such that they form a working interface with the catheter delivery device.

Once the medical device is wound down onto the delivery catheter, it is introduced into the body. The catheter is advanced in a bodily lumen to a desired location in the body and the inventive medical device is caused to expand by once again rotating the delivery catheter, but in the opposite sense of the direction it initially wound the device. This expansion increases the diameter of the medical device, and brings it close to apposition to the wall of the body lumen. The device is then released from the delivery catheter. It is preferred that the deployment of the medical device from the delivery catheter be accomplished in two distinct steps and by separate actions, as this allows the physician to accurately place the medical device before releasing it from the delivery catheter. As an aid to deploying the device from the delivery catheter, or as a means to further expand the medical device once released from the delivery catheter, a balloon may be inflated to help ensure the medical device is well apposed to the lumen.

In an embodiment of the invention, the delivery means employed to deliver the device of the invention to a desired location, comprises a mechanical delivery mechanism.

A tapering diameter can be achieved by means of simply making the helical coils of different diameters as one progresses axially along the device. However, if the means of deploying the medical device into the body is based on a delivery catheter providing relative rotation across the coils of the medical device, then the condition of different diameter helical coils will require a delivery catheter capable of individually rotating each coil section. If this is not practical, then other adjustments can be made according to this invention that will allow coils of various diameters to all reach the same final diameter in exactly the same number of rotations of the delivery catheter. There is a mathematical relation using three parameters: a) the original diameter of the helical coil, b) the number of turns initially in that coil, and c) the overall length between attachment points (links) that will predict the number of rotations that the delivery catheter must undergo for the device to reach a specific final diameter needed for insertion into the body through an introducer or other device known to those familiar with the art. By way of example, in a given device, one helical coil may initially have diameter A1, number of turns N1, and distance between links D1 and it will take exactly R rotations to bring the diameter to a final value B.

$$B = 2\sqrt{\frac{\left(\frac{\pi A_1 N_1}{\text{Cos}(\theta)}\right)^2 - D_1^2}{4\pi(N_1+R)^2}}$$

where $\theta$ is the pitch angle of the helical coil.

The next helical coil in the device may then have a different diameter A2 as required to create a tapered device. For this second coil, the number of turns and/or the distance between links can be appropriately altered such that this coil will also achieve a similar final diameter B in exactly R rotations. In this way, the entire medical device, independent of starting diameters of any given coil within said device will wind down to the same diameter with the same number of rotations of the delivery catheter. This relationship will result in non-uniform distances between links in the medical device (therefore, non-uniform attachment points to the delivery catheter), but reduces the number of required moving parts of the catheter to one moving shaft and one stationary shaft independent of the number of coils used in the medical device.

Tissue prolapse, or insufficient scaffolding is considered the biggest problem faced by helical coil based devices. The present invention addresses this unmet need by incorporating non-expandable, mesh sections attached to the device at specific locations. This mesh provides a coil-based device with all the advantages of a small closed cell design device, yet preserves the inherent advantages of a helical coil.

This invention addresses the problems of restenosis in two ways. First, the mesh is designed to reduce tissue prolapse, which can be a leading cause of restenosis; therefore, by reducing prolapse restenosis may also be reduced. The mesh also distributes the mechanical stresses much more uniformly across the luminal wall. This avoids locations in the arterial wall with sharply higher stress than surrounding areas, which has been shown to correlate with restenosis. The second way the device of this invention limits restenosis is by the ability to deliver a broad range of pharmaceutical agents, including drugs designed to be anti-restenosis, anti-inflammatory or other anti-proliferatives.

The fiber used to create the coils of this invention also possess the ability to deliver biologically derived entities and biosimilars such as but not limited to: peptides, proteins, growth factors, enzymes, cytokines, chemokines, transcription factors, nuclear proteins, porphorins, tubular proteins, and any other molecule composed in whole or in part of peptides. Additionally, families of polysaccharides, oligosaccharides, glycoproteins, and carbohydrates may be included in the fibers. Oligonucleotides, single or double stranded RNA or DNA, or other combinations of any of the above may also be included in the fibers. Also included without limiting the scope of the invention are similar molecules manufactured in non-biological processes as may be familiar to those skilled in the art.

In addition, the ability to create the fibers that compose the coils and potentially link structures from multi-component, multi-layer fiber extrusions wherein each layer or component of the fiber may incorporate one or more the above listed drug types is also covered by the present invention. This multi-component capability imparts the ability to have drug release that has directional preference. For example, if the fiber comprising the coil is extruded such that the outer half of the fiber contains drug A and the inner half contains drug B, then it is reasonable to expect that the majority of drug A would go into the wall and the majority of drug B would go into the lumen.

The device of the invention addresses delivery problems in the following way. The device of the invention alters the sense of the coil, i.e. from right hand thread to left hand thread at intervals down the length of the stent at structures known as links. A link is the point where the sense of the coil changes. The concept of reversing the sense of the coil is known in the art; however, the prior art inventions lack the concept of link structures to fill in the gaps created by the divergence of the helical coils, leaving large, unsupported areas of the luminal wall. For many clinical applications these large unsupported areas represent an untenable situation that is resolved by the concept of the link structure as described in the claimed invention.

Devices of the invention are attached to the delivery means at the distal and proximal ends of the device and at each link. The attachment of the device to the delivery means can be made using retention wires, clips, pins, pegs in holes, or any mechanical means known to those skilled in the art. The device is designed to be rotated in such a way that every-other attachment point is rotated relative to the adjacent attachment points. The fact that the coil changes sense (direction) at the links allows the entire stent to be wound down in this way by turning every other attachment point a single direction. Therefore, the device of this invention will wind down onto the catheter in very few rotations regardless of the number of coil sections. This solves the problem of dealing with an awkward delivery system. It also dramatically speeds up the delivery of the device of this invention as it reduces the number of rotations required to wind down and unwind the stent.

In contrast to the movement and jumping problems demonstrated by previously known helical coil stents and other causes of inaccurate placement of the stent, the delivery means used herein is able to unwind the device to be nearly fully apposed to the interior wall of the lumen prior to releasing the mechanical coupling between the stent and the delivery catheter. Under this scenario, the stent is positioned before it is released, allowing very accurate placement of the stent.

The problem with stent migration post implantation is solved in two ways. The first way that is unique to and a part of the invention is the mesh covering, which increases the grip that the stent has on the lumen wall. The second is the reversing sense of the coils. The concept of the link structure is a differentiating point here again, as one of the requirements of the link structure is that it exerts a force on the coils joined by that link, and this increased force increases the frictional force holding the stent to the arterial wall, thereby reducing the ability of the stent to migrate post implantation.

The problem with short lengths of the stent is also solved by the reversing sense of the coils of the stent.

The problem of low resistance to collapse under a shear load is solved by using fibers that are not round, but rather have large width to thickness ratios independent of their exact cross sectional shape.

The means of implementing a tapering stent for helical coils is a unique feature of the invention as described above by altering the number of turns per coil and/or the spacing between the attachment points.

In order to clearly understand which aspects of the above are claimed to be unique to this invention, Table 1 lists those elements of the design requirement that are uniquely satisfied by this invention.

TABLE 1

| Problem | Solution by claimed invention |
|---|---|
| Tissue Prolapse | Tissue prolapse, which can result from insufficient scaffolding, is considered the biggest problem faced by helical coil based stents. This invention addresses this unmet need by incorporating a non-expandable, non-encompassing mesh, film, sheet, or foam attached to the outside of the stent at specific locations. This mesh provides a coil stent with all the advantages of a small closed cell design stent, yet preserves the inherent advantages of a helical coil. |
| | Differentiation from prior art: The mesh of this invention differs in three important ways: 1) it is non-expandable, 2) It is non-encompassing, and 3) it is used on a self expanding stent |
| Stent Migration | Stent migration is a major problem with stents of a single helical coil, as they are able to "cork-screw" down the artery. This invention addresses this issue by two approaches, namely the mesh and reversing the sense of the winding of the stent. The mesh provides increased traction against the arterial wall and initially "blinds" the arterial wall to the coil structure within, which coil structure is the presumptive cause of "cork-screw" migration. As the mesh degrades and exposes the coil to the arterial wall, the second approach, that of reversing coil sense blocks "cork-screw" migration. This happens because those physiological forces that would induce a right hand coil to "cork-screw" down the artery would tend to dilate and "anchor" a left hand coil and visa versa. In this way the stent of this invention becomes "self-anchoring". The concept of the linking structures exerting a force on the coils and the arterial wall is also important in this regard. |
| | Differentiation from prior art: This invention differs in the requirements of the link structures that connect the coil segments. In this invention the stationary links are specifically required to not only change winding sense of the coil, but to fill in the space behind the link where the right and left hand coils diverge. Clinically, this is extremely important as the gap created between coil segments when no stationary links are present leads to the following problems when used in the human body, and specifically in the cardiovascular system: 1) increased area for tissue prolapse, 2) lack of support of the lesion, 3) reduced ability to deal with dissections, 4) reduced ability to deal with vulnerable plaque, and 5) in the case where drug elution is combined with a stent of this design, there would be a dramatic loss of drug uniformity, which can negatively impact the performance of a drug eluting stent. |
| Limited to short lengths and constant diameter | Wind down treats each coil separately and each winds down as its own unit. The stent can be as long as needed by simply adding more segments. By changing the link frequency, and/or the turns per link it is possible to create a tapered stent. |
| | Differentiation from prior art: This is the only invention that allows tapered, self expanding, helical coil based stents |

In an embodiment, a section of mesh is attached to the medical device in the following way. It is welded, glued, or otherwise attached along one full edge, for example along line A or P in FIG. 1, onto the coils at or near the end of the medical device. Other mesh sections may also be similarly attached to link structures or along the fiber at other locations across the device. The height of the mesh (as illustrated in FIG. 1) is calculated to be approximately the circumference of the medical device at its desired bodily location. For example, if the medical device were manufactured at uniform diameter of 4.0 mm, and the ideal luminal diameter for this medical device post implantation was 3.0 mm, then the height of each mesh section would be the circumference of a 3.0 mm diameter lumen, or $3\pi$ mm, and the mesh section would cover 75% of the circumference of the device in its fully expanded (as fabricated) configuration.

In another embodiment, the mesh sections may be attached to the device along two edges (both lines A and C or P and R in FIG. 1). In this embodiment, the mesh can only be attached at the distal and proximal ends (meaning the furthest and closest to the user when the device is attached to the delivery catheter) and at stationary link structures. In this embodiment, the mesh cannot be attached to the coil, or to rotating links. This embodiment removes the risk that the mesh may not be exactly in place when deployed, but does so at a loss of compliance.

In yet another preferred embodiment, the mesh is shaped as chevron UVWXYZ as shown in FIG. 1. The line U is then attached to a place on the inside of a coil or link structure of the device. One or more loops of the stent coil are passed over the mesh segment, which is then folded in half along the fold line as shown in FIG. 1, entrapping some number of loops of the coil, and bringing line X directly on top line U. Line X is then attached to the outside of the same coil or link as line U, forming a closed loop of mesh that extends from the line U around the fold line to line X. The loop of the mesh formed now provides an inner and outer mesh surface on the device.

In another embodiment, a similar outcome may be produced by starting with a trapezoidal mesh. In this case it can also be folded as described for the chevron above, likewise forming a loop of mesh that entraps one or more coils of the device. In this embodiment; however, rather then ending with a parallelogram shape after folding it results in a rhombus shape, which for most applications gives sufficient coverage of the device, and still results in mesh on both the inside and outside of the coils.

In yet other embodiments, it is possible to attach the quadrilateral or parallelogram shaped meshes to exclusively to the inner surface of the device as described above for attachment to the outside. Thus it is possible in various embodiments of this invention for the mesh to exist exclusively on the outside, exclusively on the inside, or to surround both the inside and outside of the device.

While this invention may be embodied in many different forms, there are described in detail herein specific preferred embodiments of the invention. This description is an exemplification of the principles of the invention and is not intended to limit the invention to the particular embodiments illustrated.

In an embodiment, the sum total lengths of all mesh segments may be significantly less than the total end to end length of the device. In this case, there are one or more sections of the device without any mesh covering it. This may be helpful if one is aware of anatomical reasons such as bifurcations or major branches etc where a mesh could potentially pose a risk. One could then place the device in the lumen such that the non-meshed segment contains the bifurcation. In a separate procedure it may be possible to slide the coils in such a way that the bifurcation or branch is totally unobstructed.

In another embodiment, the mesh may be replaced with a solid or perforated sheet, film or foam. The attachment of the solid sheet, film or foam would be similar to the mesh.

In one embodiment, the longitudinal axes of the coils are not collinear with respect to each other. In this embodiment, the device serves the purpose of working in both a main lumen and a side branch. In this embodiment, as in others, there is no restriction that the diameter of the two sets of coils be similar.

In an embodiment, the mesh, film, sheet, foam etc is attached to the luminal side of the fiber rather than on the outside (tissue facing side). This reversal of attachment allows the sheet, film, mesh or foam to form the inner lining of the device.

In another embodiment, multiple devices each of which is one segment long, are loaded onto one delivery catheter. The delivery catheter is capable of winding down all devices simultaneously for insertion into the body, but releasing each device individually. The operating physician then has the power to decide how many device segments will be implanted into that anatomical location.

In another embodiment, the mesh, foam, sheet or film (membrane) forms a loop, which is attached encases the medical device such that the fiber forming the helical structure is sandwiched in between an inner and outer membrane.

In one embodiment of the invention, the medical device is a stent designed for the peripheral artery system. This embodiment has been discussed at length in this invention.

In another embodiment of this invention, the medical device is used as an anchor for vein grafts. In practice, the saphenous vein is used in coronary artery bypass grafting (CABG) surgery routinely. Problems with these vascular grafts commonly initiate at the site of the anastomosis. The medical device of this invention could act as an anchor point to help heal the anastomosis and decrease surgery time, potentially increasing longevity of the graft and reducing risk associated with current medical practice.

In another embodiment of this invention, the medical device is a stent graft that could be used to treat aneurysms in a number of anatomical locations such as the aorta, as well as cerebral aneurysms.

In another embodiment of this invention, the medical device is a stent suitable for coronary applications, and specifically to address the pathological problem of vulnerable plaque.

In another embodiment of this invention, the medical device is an anchor for a vena cava filter. In this embodiment, it is likely that one segment is all that would be needed, and the design of the link would be such that the vena cava filter attached at that point, or that the link structure was composed of the filter. This would create an anchor that can be placed in flow, be non-migratory, have low restenotic response, have the ability to locally deliver drugs to the tissue of the vascular wall, and may potentially provide a simple means of implantation inside the body lumen.

In another embodiment of this invention, the medical device is an anchor for indwelling catheters that might get used for such purposes as intravascular monitoring, feeding, drug dispensing etc. Such indwelling catheters may also be used in the digestive tract as feeding tubes, during high risk pregnancy as fetal monitoring, or any other purpose known to those skilled in the art. In these embodiments, the link structure could simply include a method for attaching the indwelling catheter. In this way, it is assured that the catheter will remain well anchored, and can have a fixed position in the lumen relative to the wall at the attachment point.

In another embodiment of this invention, the medical device is an Arteriovenous (A-V) shunt anchor In another embodiment of this invention, the medical device is a Vaso-occlusive device In another embodiment of this invention, the medical device is a tracheal stent. In this embodiment, disease states such as tracheal malasia may be treated by maintaining the patency of the airway. The current most significant obstacle with treating this particular condition is that it presents at birth, but the patient requires treatment for prolonged periods. Therefore, current best practice is the insertion of a tube, but that tube must be replaced as the patient grows, and another tube inserted. It is the removal of the tube that is particularly difficult and dangerous. Therefore, a tracheal stent made from biodegradable materials may be ideal, as the old device would not need to be removed, and only the much simpler and safer operation of insertion would need to be repeated multiple times. The self expanding nature of this invention would allow some amount of patient growth prior to the device degrading.

In another preferred embodiment of this invention, the medical device is a bronchial stent.

In another preferred embodiment of this invention, the device is used in urinary tract applications. The device could be used as an adjuvant treatment to removal of kidney stones. In this case, the device maintains the patency of the ureter.

In an embodiment of this invention, the device is a stent for fallopian tubes to be used for cases where the surgical reversal of a tubal ligation becomes closed due to growth of surrounding tissues, which may happen, for example, in the case of tumors etc. Fallopian stents are also used in the surgical reversal of a tubal ligation.

In another embodiment of this invention, the medical device is a stent for the biliary system.

In another embodiment of this invention, the medical device is a stent for use in erectile dysfunction. Some 20-30% of patient who take medicines such as Viagra for erectile dysfunction do not respond to the medication. A very small stent to open the blood flow could improve these patients dramatically.

In another preferred embodiment of this invention, the medical device is used in the esophagus to treat various syndromes such as Barret's Esophagus or other conditions that may require a stent.

In another preferred embodiment of this invention, the medical device is used to treat Crohn's disease patients by maintaining an open lumen and delivering appropriate drugs to the wall of the digestive tract.

What is claimed is:

1. A device for placement in a lumen, the device comprising: a plurality of segments, wherein each segment comprises a first helical coil and a second helical coil of opposing winding sense and each segment is connected to another segment by a first structure, wherein each first structure changes the winding sense of adjacent segments, wherein each first structure comprises a cross-over point comprising an end of one of the first helical coils overlapping an end of one of the second helical coils, wherein the end of the first helical coil and the end of the second helical coil are joined, and each first structure extends into and fills a gap created by the divergence of the segments connected to each first structure, and wherein each first structure pushes the end of the first helical coil and the end of the second helical coil against a wall of the lumen and exerts force on the lumen.

2. The device according to claim 1, wherein the segments and each first structure are configured to exert forces on the wall of the lumen wherein the device is placed, and where the effect of said forces holds the device in place within the lumen.

3. The device according to claim 1, wherein the first and second helical coils of each segment are connected by a second structure.

4. The device according to claim 1, wherein the device comprises a covering.

5. The device according to claim 4, wherein the covering comprises a mesh, sheet, cloth, foam or film.

6. The device according to claim 1, comprising a covering that spans a length of the device from one end to the other and is attached to varying locations on the device including but not limited to at or near ends of the device, at or near each first structure of the device, or at any other location.

7. The device according to claim 6, wherein the covering is attached to the device along an edge of the covering.

8. The device according to claim 6, wherein the covering is attached to the device along opposite edges of the covering.

9. The device according to claim 6, wherein the covering comprises drugs.

10. The device according to claim 1, wherein the plurality of segments comprise one or more drugs that are configured to be released into the lumen or into the wall of the lumen.

11. The device according to claim 1, wherein a diameter of the device is constant along its length.

12. The device according to claim 1, wherein a diameter of the device varies along its length.

13. A system comprising a delivery means, wherein the delivery means is removably connected to the device of claim 1.

14. The system according to claim 13, wherein the delivery means releases one or more of the devices at a specific location within a lumen.

15. The system according to claim 13, wherein the delivery means comprises one or more catheters.

16. The system according to claim 13, wherein the delivery means comprises a mechanical delivery mechanism.

* * * * *